(12) United States Patent
Barry et al.

(10) Patent No.: US 6,852,108 B2
(45) Date of Patent: Feb. 8, 2005

(54) APPARATUS AND METHOD FOR RESECTING AND REMOVING SELECTED BODY TISSUE FROM A SITE INSIDE A PATIENT

(75) Inventors: Robert Lawrence Barry, Kirkland, WA (US); Lauri J. DeVore, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 41 days.

(21) Appl. No.: 10/146,444

(22) Filed: May 14, 2002

(65) Prior Publication Data

US 2003/0216730 A1 Nov. 20, 2003

(51) Int. Cl.[7] ............................................... A61B 18/18
(52) U.S. Cl. ............................ 606/41; 606/45; 606/46; 604/21
(58) Field of Search ........................ 606/41, 42, 45–51; 604/21, 22

(56) References Cited

U.S. PATENT DOCUMENTS

| | | | |
|---|---|---|---|
| 5,111,828 A | | 5/1992 | Kornberg et al. |
| 5,456,689 A | * | 10/1995 | Kresch et al. ............... 606/180 |
| 5,490,860 A | * | 2/1996 | Middle et al. ............... 606/171 |
| 5,810,806 A | * | 9/1998 | Ritchart et al. ............... 606/45 |
| 6,053,877 A | | 4/2000 | Banik et al. |
| 6,086,543 A | | 7/2000 | Anderson et al. |
| 6,142,957 A | | 11/2000 | Diamond et al. |
| 6,213,957 B1 | | 4/2001 | Milliman et al. |
| 6,277,083 B1 | | 8/2001 | Eggers et al. |
| 6,280,398 B1 | | 8/2001 | Ritchart et al. |

2003/0181890 A1 * 9/2003 Schulze et al. ............... 606/1

FOREIGN PATENT DOCUMENTS

WO WO PCT/US01/51235 9/2002
WO WO PCT/US02/12325 11/2002

OTHER PUBLICATIONS

International Search Report for PCT/US03/05921, filed on Feb. 26, 2003 in 5 pages.
J&J Gateway LLC Web Page: Steps in the MAMMOTOME Surgical Procedure; Surgical Technique, Dec. 28, 2001; p1–3.

* cited by examiner

Primary Examiner—Rosiland Rollins
(74) Attorney, Agent, or Firm—Knobbe, Martens, Olson & Bear, LLP

(57) ABSTRACT

An electrosurgery device according to an embodiment of the invention captures a lymph nodule and resects it. The lymph node is captured with a vacuum and resected it with an electrode, which minimizes bleeding and limits the potentially malignant node from coming into contact with surround tissue as it is resected and removed. This limits the potential for inadvertent cancer spread. An electrosurgery device according to an embodiment of the invention also allows several lymph nodes to be resected in a single procedure, each lymph node being easily indexed according to its nodal station and stored in a manner that limits the potential for cross-contamination. An electrosurgery device according to an embodiment of the invention further provides a collector for individually receiving resected lymph nodes. The collector may be easily detached and sent to pathology without interrupting resection of other lymph nodes.

12 Claims, 17 Drawing Sheets

APPARATUS AND METHOD FOR RESECTING AND REMOVING SELECTED BODY TISSUE FROM A SITE INSIDE A PATIENT

FIELD OF THE INVENTION

The present invention is generally directed to an apparatus and method for resecting body tissue from a site within a patient and removing it from the patient. The present invention is more particularly directed to an electrosurgery apparatus for capturing, resecting, removing, and indexing selected body tissue, such as lymph nodes or other tissue.

BACKGROUND

One important step in the treatment of pulmonary cancer is resecting bronchial lymph nodes. Mediastinoscopy is one frequently employed procedure to resect lymph nodes in the thorax and bronchial system. An incision is made in the sternal or jugular notch at the base of the neck, and a tubular instrument called a mediastinoscope is inserted in the incision, placed between the trachea and the sternum, and directed into the chest cavity. The mediastinoscope permits direct visualization of the lymph nodes located in the paratracheal and parabronchial areas. The size of the instrument is large enough to allow the insertion of shearing and grabbing tools to resect regional lymph nodes. Once removed, the resected lymph nodes are sent to pathology for analysis.

The procedure for bronchial lymph node visualization and resection through the mediastinoscope has problems. For example, the procedure is limited to taking one lymph node at a time. Since a plurality of lymph nodes are generally required to be resected, the procedure can be relatively long. In addition, the instrumentation to grab and resect the lymph node may cause problems. For example, surgeons generally utilize long instruments such as ring forceps to suspend the target lymph node to be resected and removed. Such instruments can result in potential squeezing and damage to lymph nodes that may contain cancer cells, thus causing bleeding and releasing potentially hazardous byproducts such as tissue, blood, and cells into the chest cavity. Obviously, this is a condition to be avoided. Removing these hazardous byproducts from the patient is a problem. Another problem stems from the very narrow working channel and the close proximity of vulnerable structures such as arteries and the heart. Traditional biopsy and resection devices may impact the adjacent structures. The number of samples generally taken causes a storage problem and a cross-contamination problem. With present procedures and devices, each sample is individually removed and indexed according to its nodal station before being sent to pathology. This requires time and effort.

Hence, there is a need in the art for an improved apparatus and method for resecting a selected body tissue, such as bronchial and thoracic lymph nodes. More particularly, there is such a need for a device and method for quickly and efficiently capturing bronchial and thoracic lymph nodes, resecting them without causing bleeding or spilling byproducts into the patient, and indexing them. The present invention addresses that need.

SUMMARY

The present invention provides a device for resecting selected body tissue from other body tissue at a site inside a patient and removing the selected body tissue. The device includes an electrosurgery device having an electrode that cuts through tissue to resect the selected body tissue from the other body tissue, a tubular member having a vacuum lumen that draws the selected body tissue into proximity with the electrode to permit the electrode to resect the selected body tissue from the other body tissue, and a collector that receives the resected body tissue. The device may further include a compliant port through which the selected body tissue is drawn, and that maintains a seal with the selected body tissue. The compliant port may include a flexible material carried on the tubular member and having an opening maintaining a vacuum against the other body tissue and resection byproducts when the selected body tissue has been resected. The collector may also receive resection byproducts. The collector may be in vacuum communication with the lumen. The vacuum lumen may draw the resected body tissue into the collector. The electrode may be an active electrode of an electrosurgery system. The electrode may form an RF blade, and may form an RF loop. The electrode may be a bipolar device. The electrode may be a monopolar device. The collector may include at least one collection chamber. The collector may comprise a plurality of collection chambers, each of which is selectively communicable with the vacuum lumen. The collection chamber may have reference markings. The collector may be disengaged from the device after receiving the resected body tissue. The collector may be disengaged from the device after receiving the resected body tissue and another collector may be engaged with the device to receive another resected body tissue. The tubular member may be curved at its distal tip. The distal tip may be shaped to accommodate a particular anatomy.

The present invention further provides a device for resecting selected body tissue from other body tissue at a site inside a patient and removing the selected body tissue. The device resecting selected body tissue includes an electrosurgery device having an electrode that cuts through tissue to resect the selected body tissue from the other body tissue, a tubular member having a vacuum lumen that draws the selected body tissue into proximity with the electrode to permit the electrode to resect the selected body tissue from the other body tissue, a compliant port carried on the tubular member through which the selected body tissue is drawn, and that maintains a seal with the selected body tissue, and a collector having a plurality of collection chambers, each of which is selectively communicable with the vacuum lumen to receive the resected body tissue.

The present invention still further provides a method of resecting selected body tissue from other body tissue at a site inside a patient and removing the selected body tissue. The method includes the steps of disposing a tubular member having a lumen adjacent to the selected body tissue, creating a vacuum inside the lumen to draw the selected body tissue inside the lumen, drawing the selected body tissue inside the lumen with a vacuum, cutting through tissue to resect the selected body tissue from the other body tissue with an electrosurgery device, and collecting the resected body tissue in a collector. The method may include the further step of aspirating the selected body tissue from the patient out of another end of the lumen. The method may include the further step of drawing the selected body tissue with the vacuum through a compliant port that maintains a seal with the selected body tissue. The compliant port may include a flexible material carried on the tubular member and having an opening maintaining a vacuum against the other body tissue. The step of collecting the resected body tissue may include the further step of collecting resection byproducts.

The present invention further includes a device for resecting selected body tissue from other body tissue at a site inside a patient and removing the selected body tissue. The device includes electrosurgery means for resecting the selected body tissue from the other body tissue, vacuum directing means for drawing the selected body tissue into proximity with the electrosurgery means to permit the electrosurgery means to resect the selected body tissue from the other body tissue, and collection means for receiving the resected body tissue.

These and various other features as well as advantages which characterize the present invention will be apparent from a reading of the following detailed description and a review of the associated drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify identical elements, and wherein:

DETAILED DESCRIPTION

Figure 1:
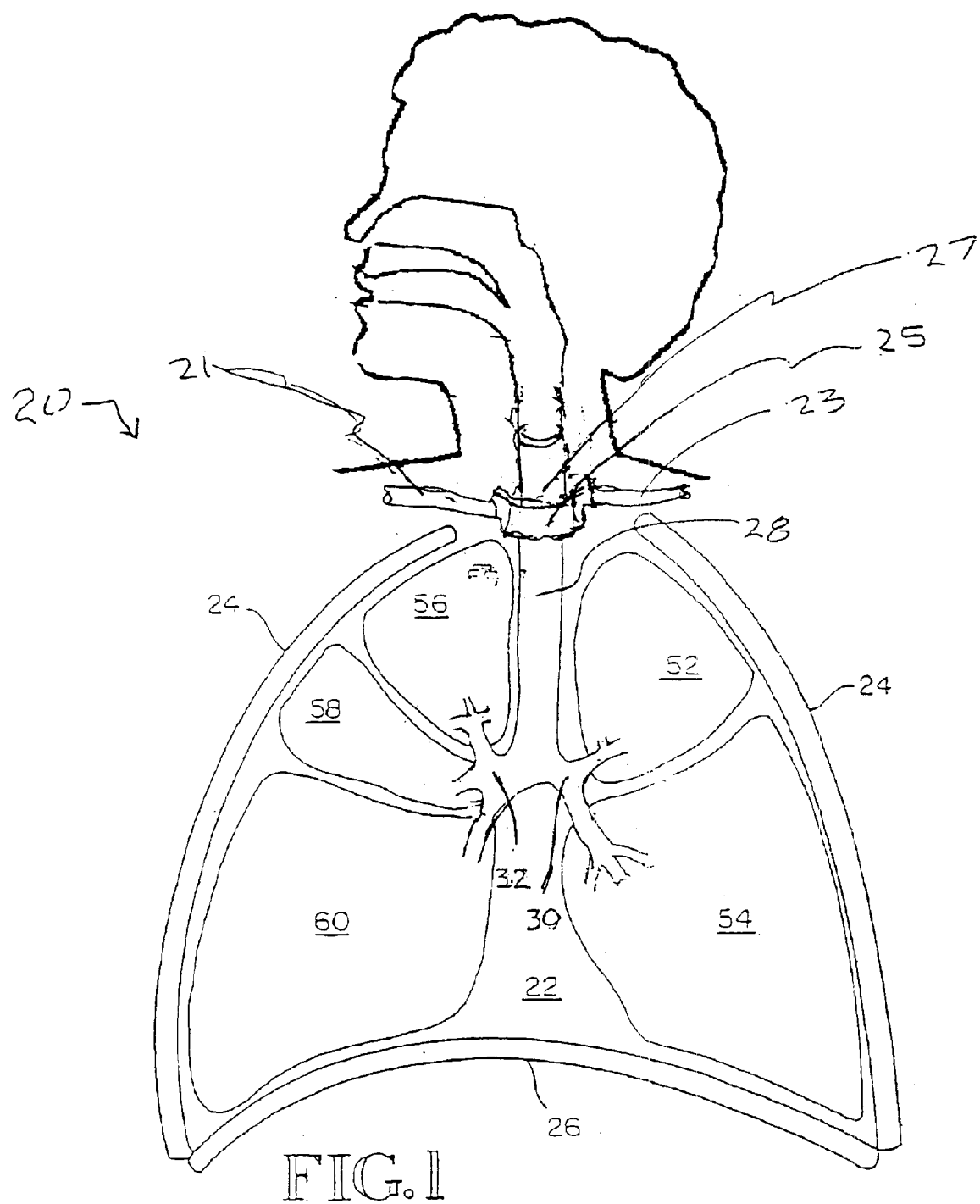
FIG. 1 illustrates a person's neck, collarbones, and respiratory system.

In the following detailed description of exemplary embodiments of the invention, reference is made to the accompanying drawings that form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined only by the appended claims.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicated like parts throughout the views. Additionally, a reference to the singular includes a reference to the plural unless otherwise stated or inconsistent with the disclosure herein.

Briefly stated, an electrosurgery device according to an embodiment of the invention described captures a lymph nodule and resects it. The lymph node is captured with a vacuum and resected with an electrode, which minimizes bleeding and limits the potentially malignant node from coming into contact with surrounding tissue as it is resected and removed. This limits the potential for inadvertent cancer spread. An electrosurgery device according to an embodiment of the invention also allows several lymph nodes to be resected in a single procedure, each lymph node being easily indexed according to its nodal station and stored in a manner that limits the potential for cross-contamination. An electrosurgery device according to an embodiment of the invention further provides a collector for individually receiving resected lymph nodes. The collector may be easily detached and sent to pathology without interrupting resection of other lymph nodes.

FIG. 1 illustrates a person's neck, collarbones, and respiratory system. The respiratory system 20 resides within the thorax 22 that occupies a space defined by the chest wall 24 and the diaphragm 26.

The respiratory system 20 includes the trachea 28, the left mainstem bronchus 30, the right mainstem bronchus 32, which then further divides into bronchial branches and sub-branches. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof.

The right clavicle 21 and the left clavicle 23 join at the top of the sternum 25 (only the top portion of sternum 25 is shown for clarity) and lie anteriorly to the trachea 28. A sternal or jugular notch 27 is formed in the sternum 25 and at the base of the neck.

Figure 2:
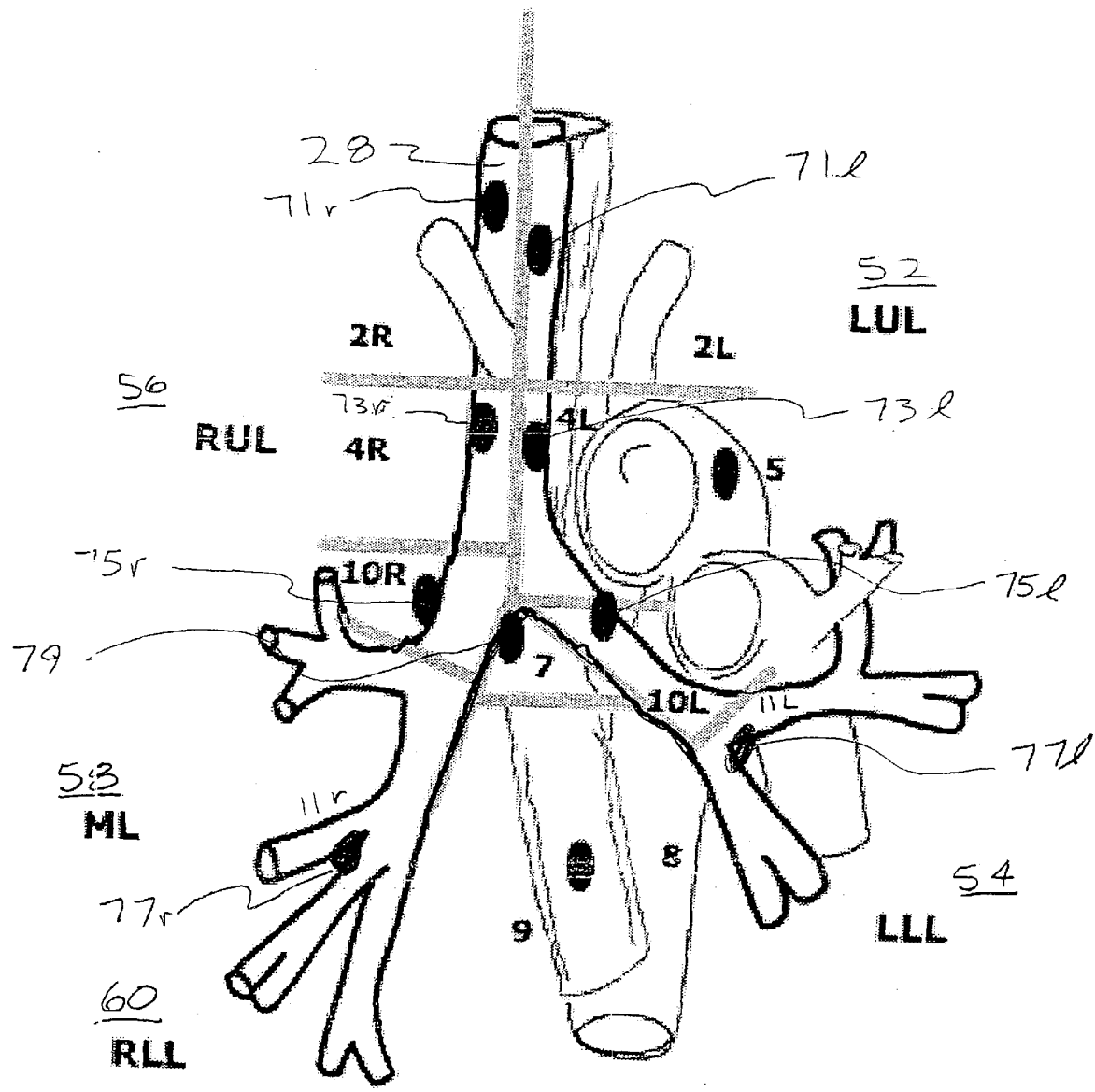
FIG. 2 illustrates several of the lymph nodes of the respiratory system.

FIG. 2 illustrates several of the lymph nodes of the respiratory system. The nodes have been classified into regional nodal stations for lung cancer staging, and the stations are used to index biopsied or resected lymph nodes. FIG. 2 illustrates right and left upper paratracheal nodes 71r and 71l (indexed as stations 2R and 2L); right and left lower paratracheal nodes 73r and 73l (indexed as stations 4R and 4L); right and left tracheo-bronchial angle nodes 75r and 75l (indexed as stations 10R and 10L); right and left interlobar nodes 77r and 77l (indexed as stations 11R and 11L); and subcarinal node 79 (indexed as station 7). Typically, several lymph nodes may be located at one station. Additional nodes and stations were omitted from FIG. 2 for clarity.

Figure 3:
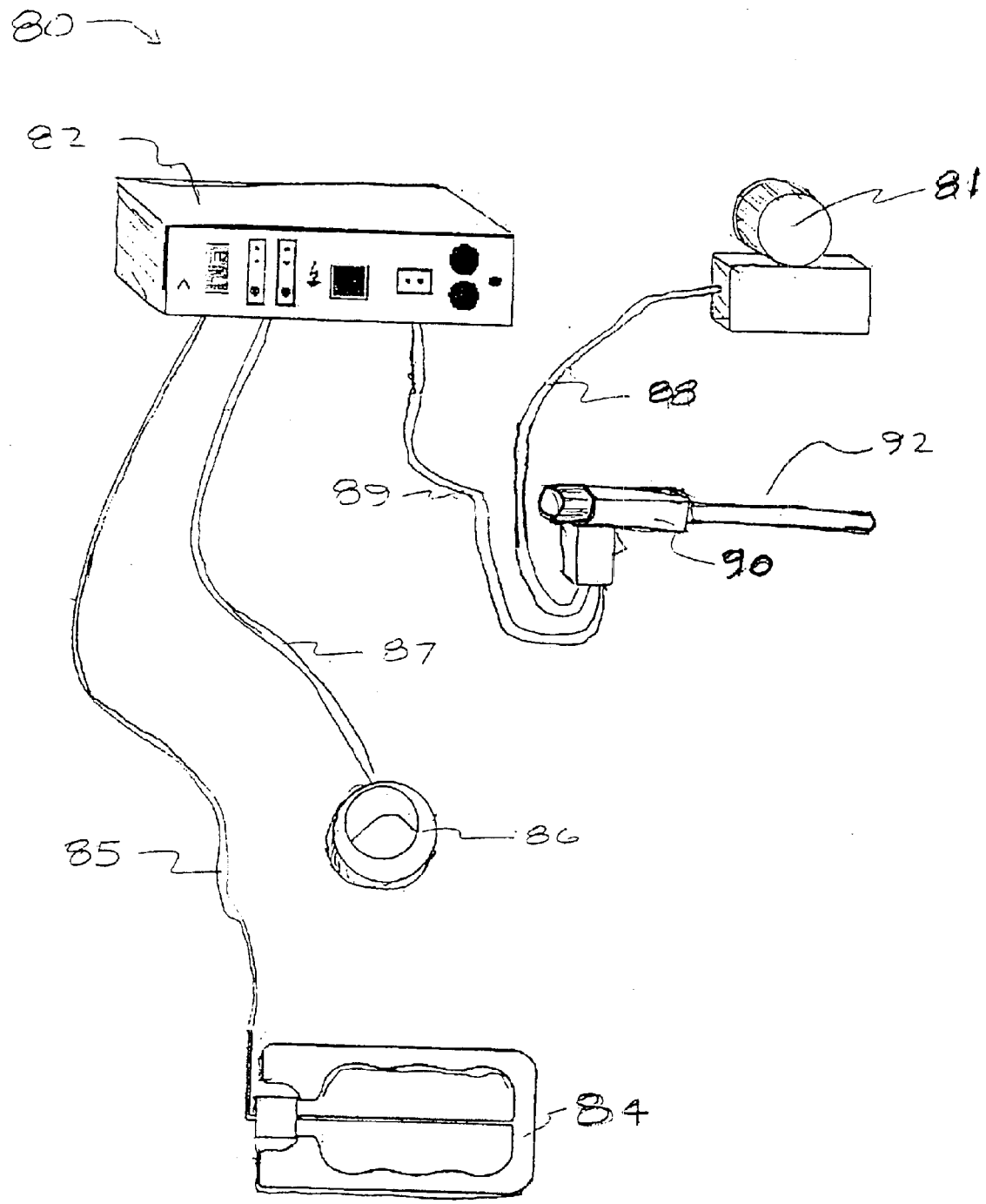
FIG. 3 illustrates a monopolar electrosurgery system suitable for use with an electrosurgery device to resect body tissue at a site within a patient, in accordance with the present invention.

FIG. 3 illustrates a monopolar electrosurgery system suitable for use with an electrosurgery device to resect body tissue at a site within a patient, in accordance with the present invention. Electrosurgery system 80 includes an aspiration pump 81, an electrosurgery RF generator 82, a ground electrode 84, a ground electrode coupler 85, a foot control unit 86, a foot control unit coupler 87, an aspiration coupler 88, an electrosurgery coupler 89, and an electrosurgery device 90 including a tubular member 92. The depiction of a monopolar electrosurgery system in FIG. 3 is not intended to limit the practice of the present invention to only monopolar devices. In an alternative embodiment of the invention, a bipolar electrosurgery system may be used, eliminating the need for ground electrode 84 and ground electrode coupler 85.

Electrosurgery RF generator 82 is coupled to ground electrode 84 by ground electrode coupler 85, to foot control unit 86 by foot control unit coupler 87, and to electrosurgery device 90 by electrosurgery coupler 89. Electrosurgery device 90 includes an active electrode (not shown) and tubular member 92. Aspiration pump 81 is coupled to electrosurgery device 90 and to tubular member 92 by aspiration coupler 88.

In operation, electrosurgery RF generator 82 supplies a source of electrical current, typically in the radio frequency range, to the active electrode of electrosurgery device 90 and ground electrode 84 (which is sometimes known as a dispersive electrode). The current forms an electrical arc ahead of the active electrode and volatizes the tissues, separating them as if they were cut. Ground electrode 84 provides a large surface for patient electrical contact, and is placed in electrical contact with the patient. The active electrode directs the current flow into the tissue of the patient, and ground electrode 84 directs current flow from the patient to electrosurgery generator. The current waveform supplied by electrosurgery RF generator 82 may vary in strength and frequency, and it may be pulsed. The RF energy may be modulated in a sinusoidal or square waveform. It may also be mixed mode or combination thereof. The particular electrosurgery current waveform is selected to accomplish the objectives of the procedure being performed. The surgeon may use foot control unit 86 to control electrosurgery RF generator 82 or a hand controlled switch on electrosurgery device 90.

Tubular member 92 has a vacuum lumen for drawing selected body tissue into proximity to the active electrode, and for aspirating the resected tissue from the patient. Tubular member 92 carries the active electrode. Electrosurgery device 90 is configured to be carried in a conduit or catheter of an endoscope, such as a mediastinoscope, or alternatively may be used separately in conjunction with an endoscope or other viewing device.

Figure 4:
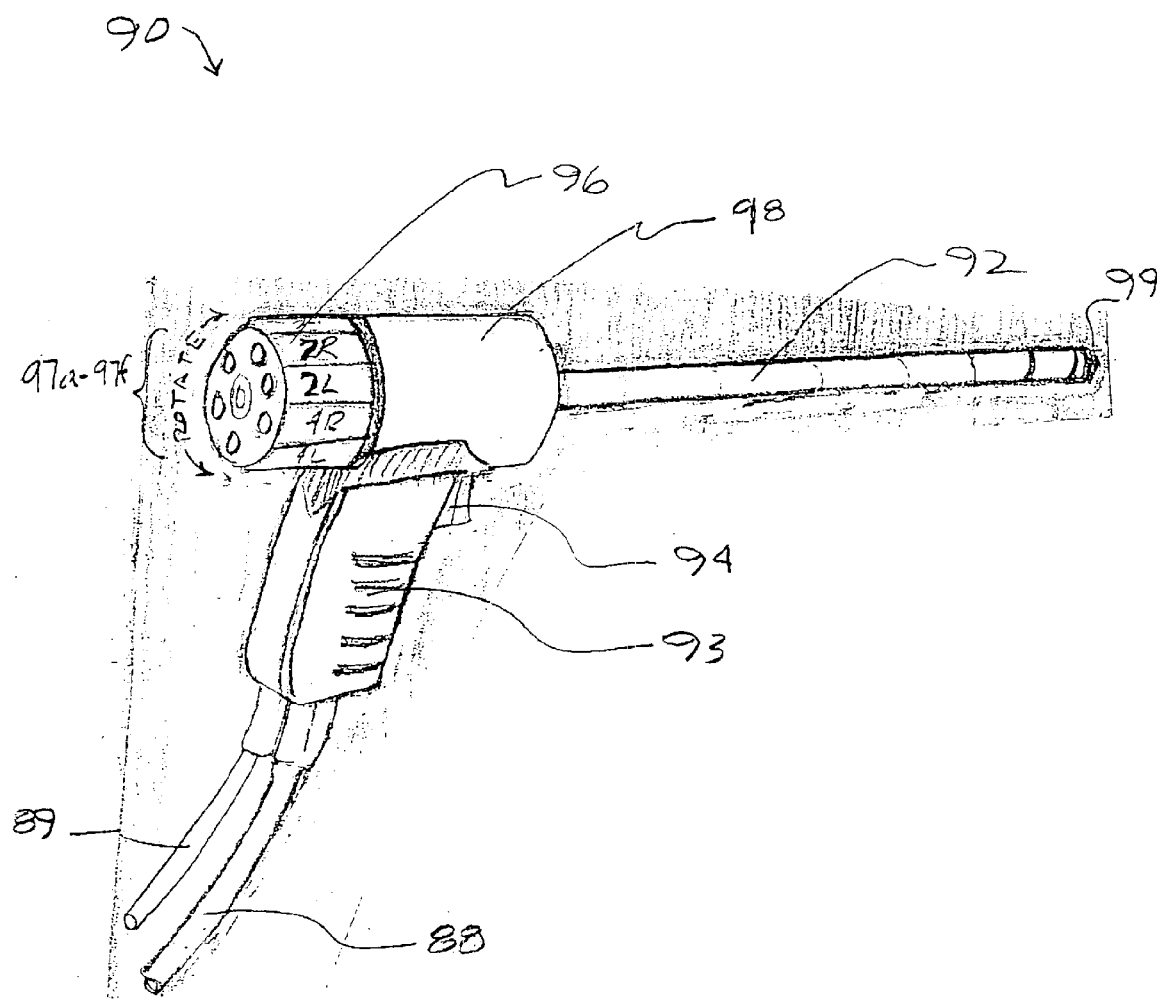
FIG. 4 is a perspective view of an electrosurgery device, in accordance with the present invention.
Figure 5:
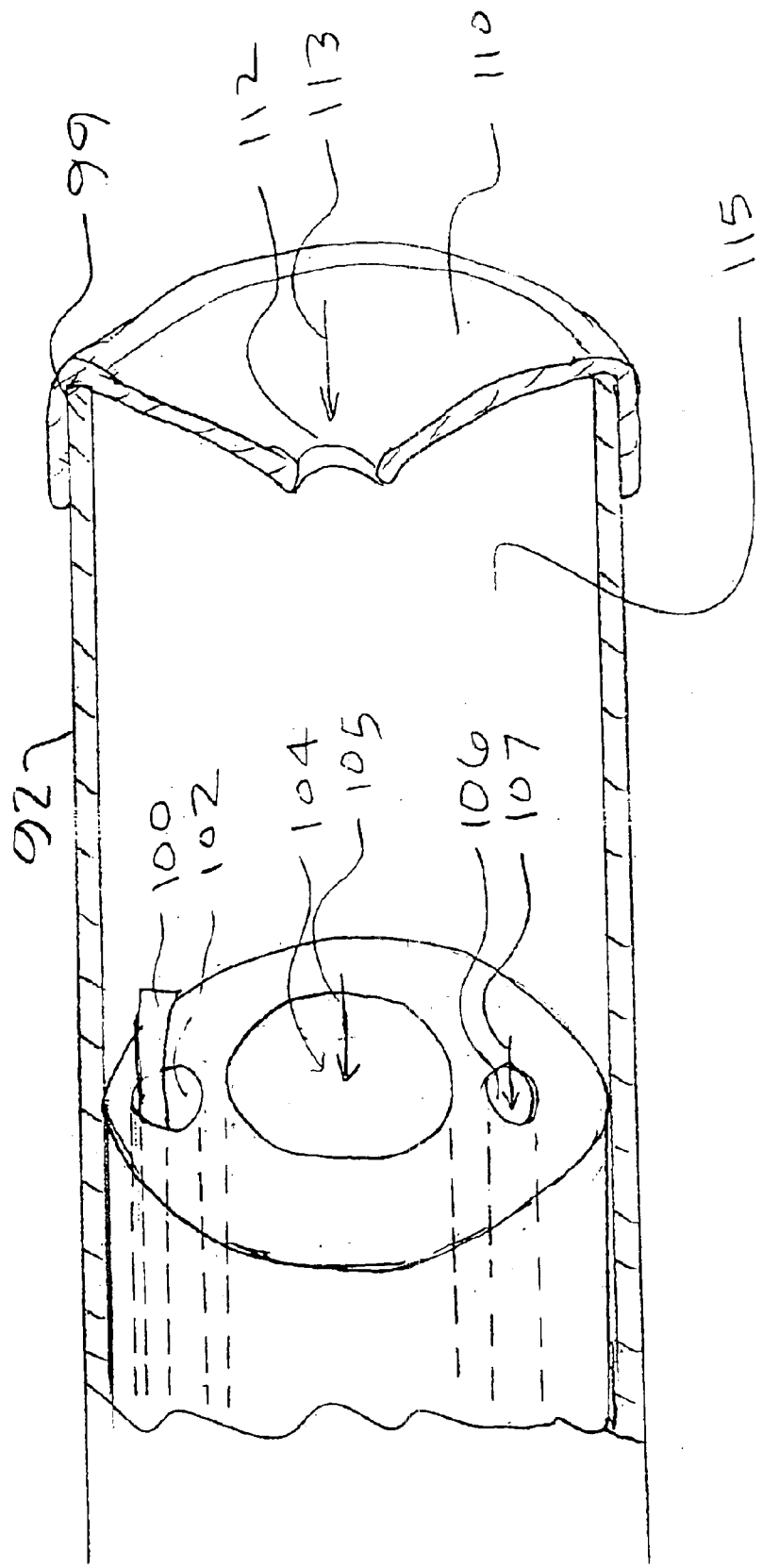
FIG. 5 is a partial longitudinal section view of the distal tip of the tubular member of the electrosurgery device of FIG. 4, according to an embodiment of the invention.

FIG. 4 is a perspective view of electrosurgery device 90, in accordance with the present invention. FIG. 5 is a partial longitudinal section view of the distal tip 99 of the tubular member 92 of the electrosurgery device 90 of FIG. 4, in accordance with the present invention. Electrosurgery device 90 includes a body 98, a tubular member 92, a handle 93, an activation device 94, and a collector 96 having chambers 97a–97f. Tubular member 92 includes a distal tip 99, an electrode 100, an electrode lumen 102, a primary vacuum lumen 104, a secondary vacuum lumen 106, a compliant port 110, and a resection lumen 115.

Body 98 carries tubular member 92, handle 93, activation device 94, and collector 96. Aspiration coupler 88 and electrosurgery coupler 89 are coupled to electrosurgery device 90 at handle 93 in a preferred embodiment. Aspiration coupler 88 is in vacuum communication with collector 96, and lumens 102 and 104. Collector 96 is in vacuum communication with lumens 102 and 104. Collector 96 can be disengaged from body 98, and another collector 96 can be engaged with body 98 without electrosurgery device 90 being removed from a patient. Collector 96 may have a plurality of selectable chambers, each chamber being selectively communicable with vacuum lumens 102 and 104. In a preferred embodiment, collector 96 has six chambers, 97a–97f, and is arranged much like a cylinder on a six-shot revolver, with collector 96 being rotatable to select a chamber, and removable and replaceable. Chambers 97a–97f are indexed or reference marked corresponding to the lymph node stations likely to be encountered. For example, collector 96 is reference marked for the upper and lower paratracheal nodes, stations 2R, 2L, 4R and 4L, in the embodiment illustrated.

Electrode 100 is carried in lumen 102 of tubular member 92, is exposed to resection lumen 115, and is coupled to the electrosurgery generator by electrode coupler 89. In a preferred embodiment, electrode 100 is an active electrode in the shape of a blade, and consisting of radio frequency surgical materials suitable for cutting through tissue, including resecting selected tissue such as lymph nodes from other body tissue. In an alternative embodiment, electrode 100 may be sharpened. The electrode may be maneuverable. Electrode 100 may be carried substantially within lumen 102 until needed, and then extended for use.

Figure 10:
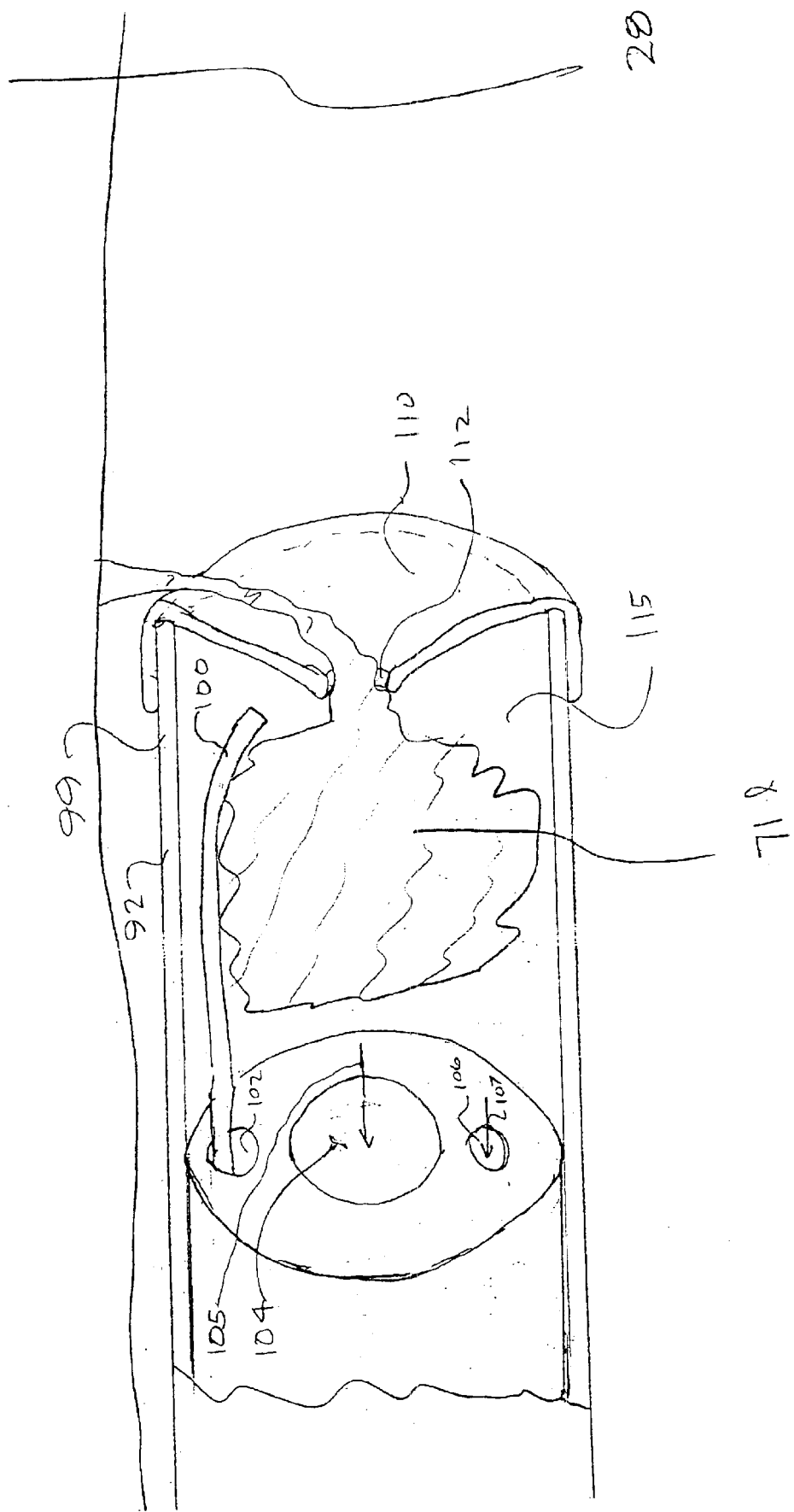
FIG. 10 illustrates an intermediate step where the electrode has been partially deployed and moved centrally.
Figure 11:
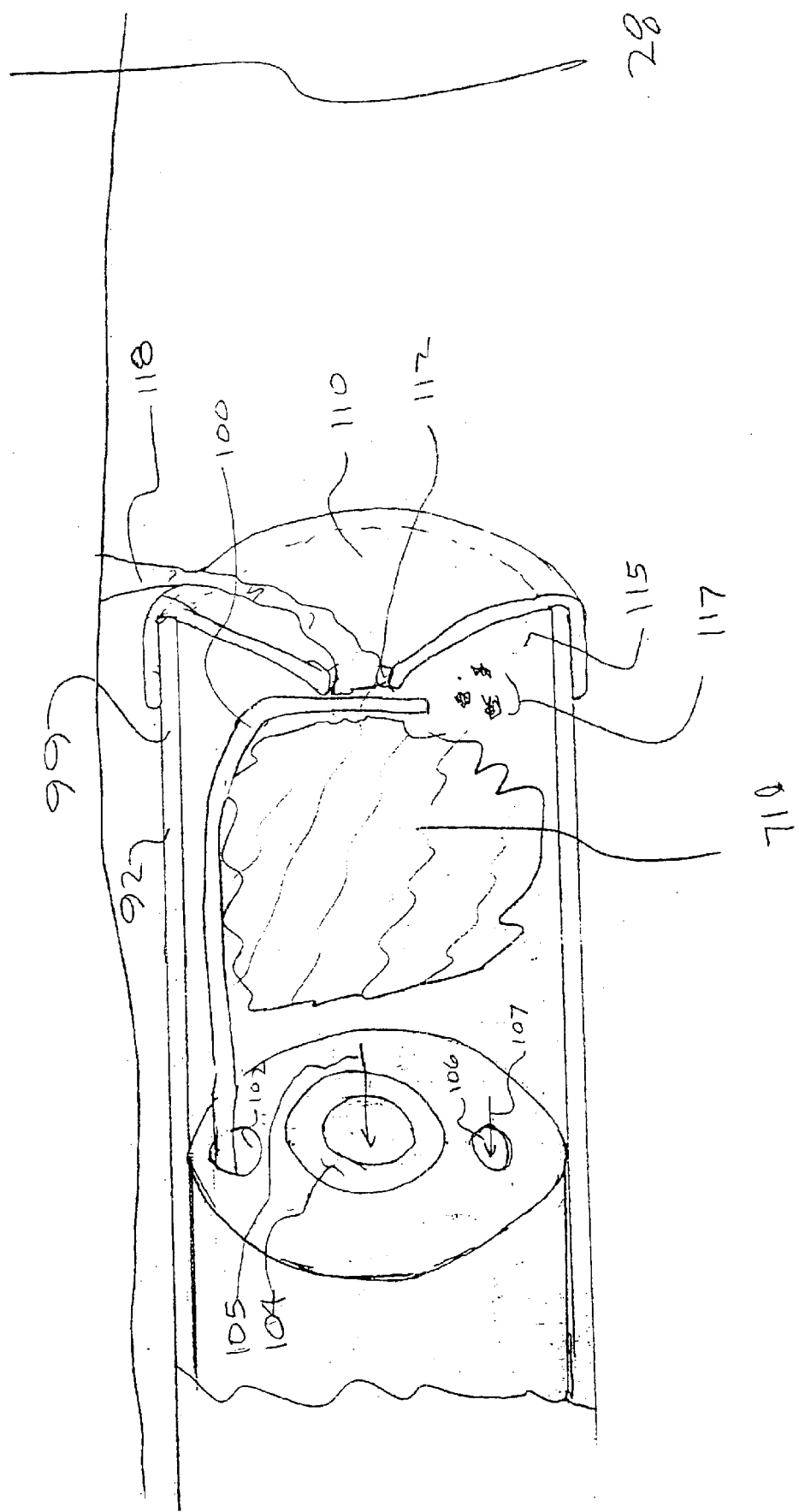
FIG. 11 illustrates an intermediate step where the electrode has cut through tissue to resect the lymph node from other body tissue.

Activation device 94 is a trigger-like device used to extend electrode 100 for cutting and to retract it. FIGS. 10 and 11 illustrate extension of electrode 100 for cutting.

Tubular member 92 may be made of any material suitable for surgical use. When the electrosurgery device 90 is a bi-polar device, the tubular member 90 may be any material suitable for surgical use and for forming a return electrode. One end is coupled to body 98, and the other end including distal tip 99 is arranged for insertion into an incision in the sternal notch and down into the thorax. While illustrated as round in FIG. 5, distal tip 99 can be any cross-sectional shape suitable for the purpose of electrosurgery device 90. FIGS. 16–19 illustrate alternative shaped embodiments of the distal tip 99. In an alternative embodiment, the distal tip 99 may be arranged for insertion through an incision in another part of the body. For example, lymph nodes at stations 7, 8, and 9 of FIG. 2 can only be reached by entry between certain ribs. While distal tip 99 is illustrated as lying in a single plane perpendicular to the longitudinal axis of tubular member 92, it may be formed at another angle and/or in multiple planes to facilitate access to lymph nodes. In an alternative embodiment, distal tip 99 may have a bend or curve to facilitate access to lymph nodes. Tubular member 92 includes lumen 102 for delivery of electrode 100. Tubular member 92 also includes primary vacuum lumen 104 and secondary vacuum lumen 106 providing vacuum draws 105 and 107 in the resection lumen 115. In an alternative embodiment, a plurality of secondary vacuum lumens 106 may be provided. In another alternative embodiment, electrosurgery system 80 includes a system providing a saline solution to electrosurgery device 90, and tubular member 99 includes a lumen that provides the saline solution to assist in RF cautery and for cooling.

The compliant port 110 includes the opening 112 and is carried on the distal tip 99. The complaint port 110 may be made from a flexible material such as silicone. The opening 112 is flexible to allow a wide range of lymph node sizes to be drawn through, while maintaining a vacuum seal against the lymph node. The vacuum draws 105 and 107 provide the vacuum draw 113 through the opening 112.

Figure 6:
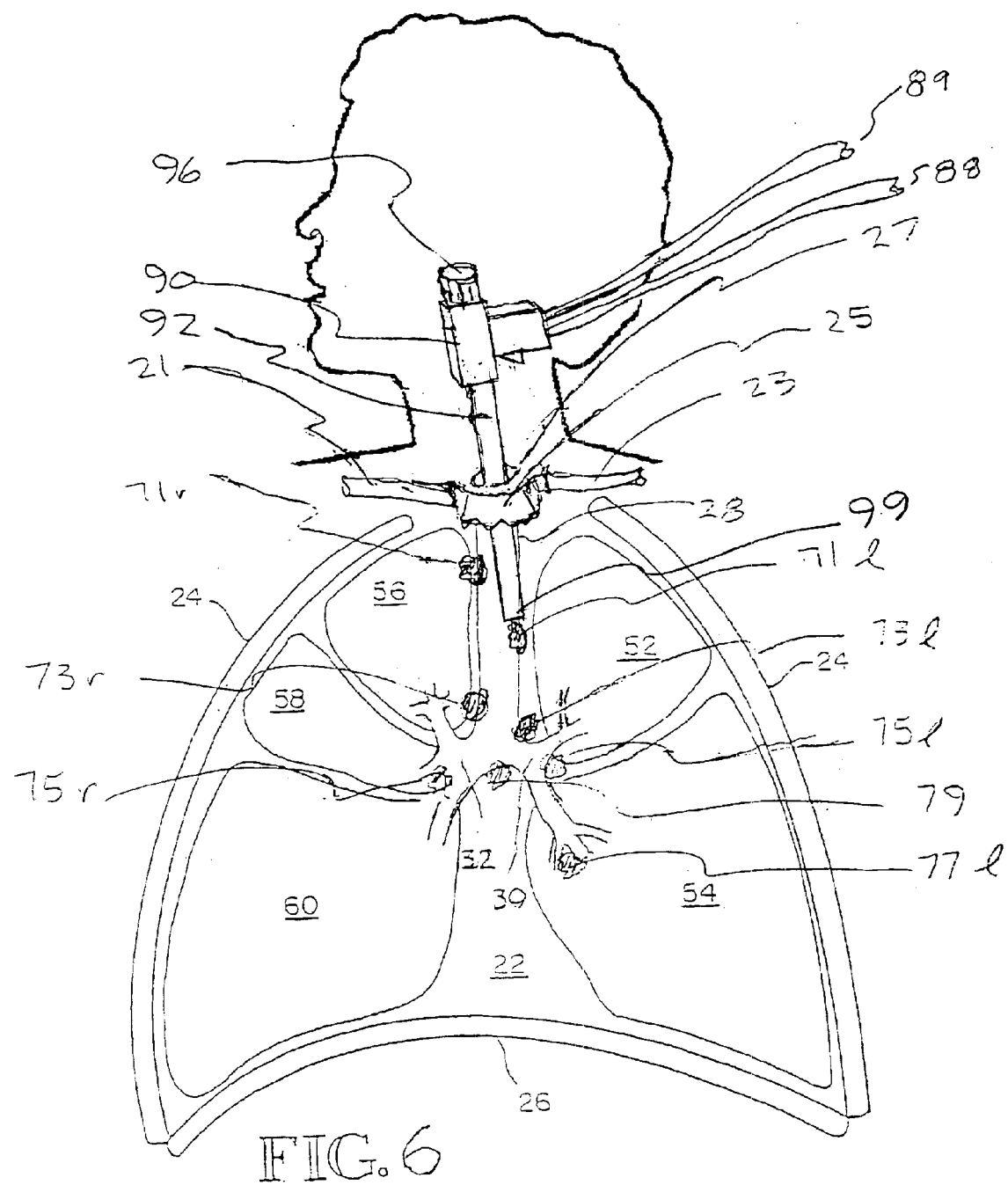
FIG. 6 illustrates an electrosurgery device inserted through an incision in the sternal notch and into a thorax, in accordance with the invention.

FIG. 6 illustrates an electrosurgery device inserted through an incision in the sternal notch and into a thorax, in accordance with the present invention. FIG. 6 depicts the tubular member 92 of electrosurgery device 90 inserted through an incision at the sternal notch 27 just above the sternum 25. The procedure for placing the tubular member 92 involves anesthetizing the patent, making an incision at the sternal notch 27 just above the sternum 25, and inserting tubular member 92 through the incision and between the trachea 28 and the top of the sternum 25. Tubular member 92 is advanced to where its distal tip 99 is adjacent to lymph node 71*l* or any other selected lymph node. Electrosurgery device 90 may be incorporated into another device that provides viewing of the selected lymph nodes, or may be accompanied in use by a viewing device.

Figure 7:
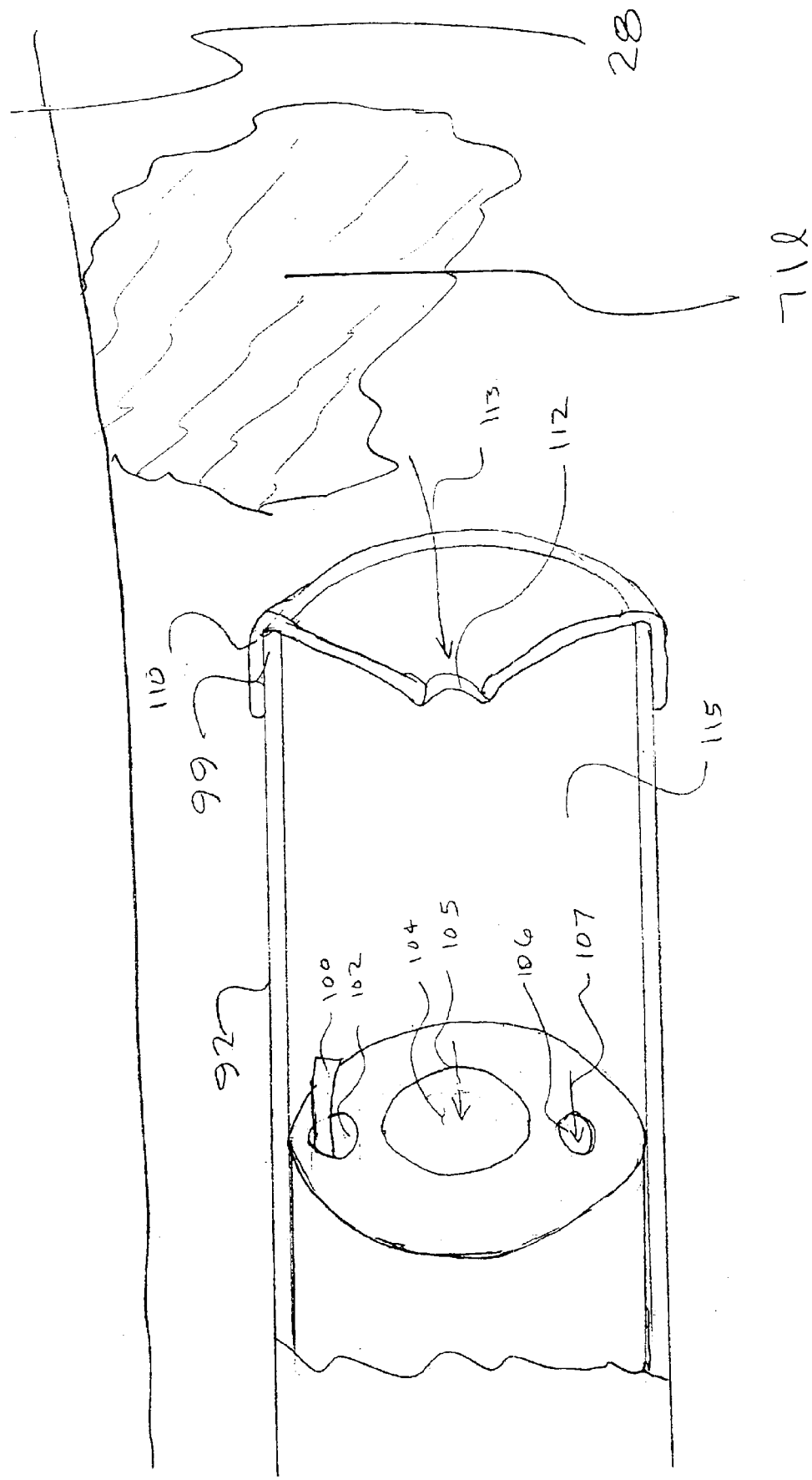
FIG. 7 illustrates a step in resecting a lymph node where the distal tip of the tubular member is adjacent to a lymph node for resection, in accordance with the present invention.

FIGS. 7–12 illustrate several steps in resecting a lymph node, in accordance with the present invention. FIG. 7 illustrates the distal tip 99 of tubular member 92 adjacent to lymph node 71*l* for resection. Vacuum draw 113 creates a vacuum drawing lymph node 71*l* toward opening 112 in compliant port 110. Vacuum draw 113 may be used to gently tease the lymph node 71*l* out from adjacent tissues, and move it toward opening 112.

Figure 8:
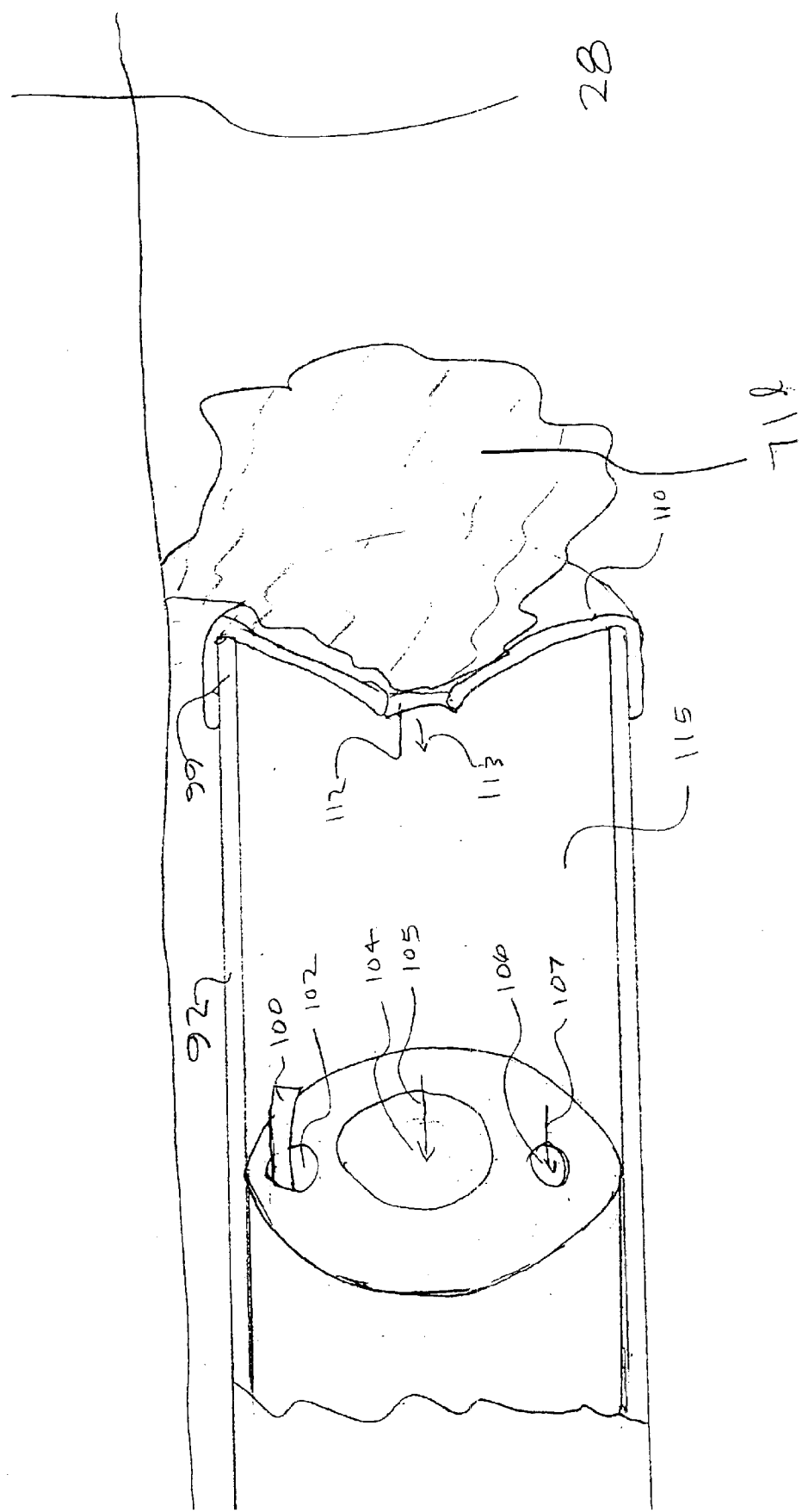
FIG. 8 illustrates an intermediate step where a lymph node has been drawn in proximity to the compliant port by the vacuum draw.
Figure 9:
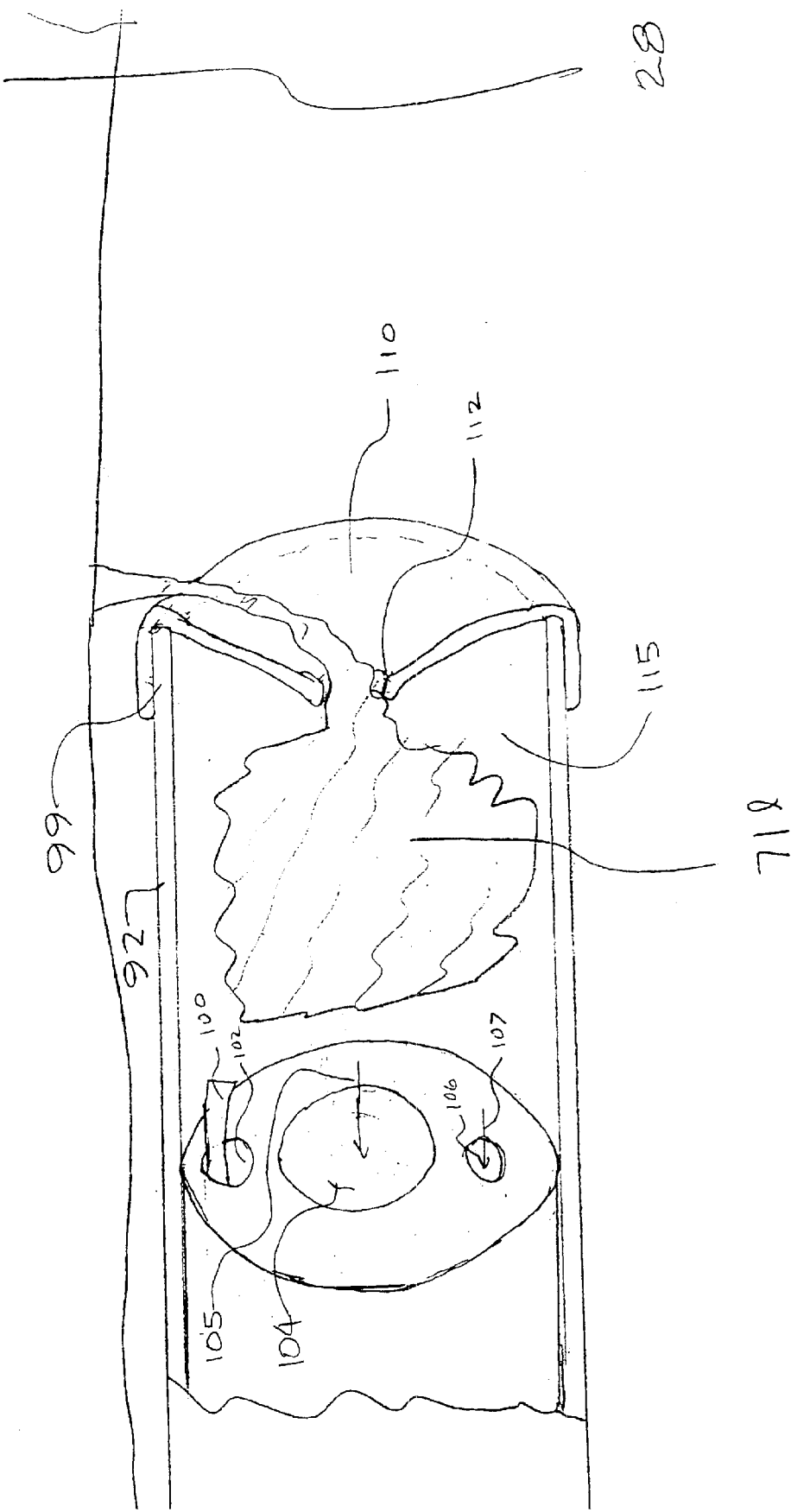
FIG. 9 illustrates an intermediate step where the lymph node has been drawn substantially through the compliant port and into the resection lumen.

FIG. 8 illustrates lymph node 71*l* having been drawn in proximity to compliant port 110 by vacuum draw 113. FIG. 9 illustrates lymph node 71*l* having been drawn substantially through compliant port 110 by vacuum draw 113 (not shown) and by vacuum draws 105 and 107, into resection lumen 115. In this position, lymph node 71*l* is in proximity with electrode 100, permitting it to be resected. Compliant port 110 and opening 112 maintain a seal with lymph node 71*l*, causing a vacuum in resection lumen 115. FIG. 10 illustrates electrode 100 having been partially deployed toward lymph node 71*l* and moved centrally. Electrode 100 may be deployed by squeezing the activation device 94 of FIG. 4. FIG. 11 illustrates electrode 100 having been fully deployed and activated to cut through tissue at a location near opening 112 to resect lymph node 71*l* from other body tissue 118. Activation of the electrode may be by further squeezing the activation device or by using foot control unit 86 of FIG. 2. Vacuum draws 105 and 107 continue to maintain a vacuum in resection lumen 115 against the seal with lymph node 71*l* provided by compliant port 110 and opening 112. Using an electrosurgery device such as electrode 100 minimizes bleeding and release potentially hazardous tissue, blood, and cells (hereafter referred to as "resection byproducts 117"). If any resection byproducts 117 are created, the vacuum maintained in resection lumen 115 retains the byproducts 117, and limits any escape into the chest cavity. Until vacuum draws 105 and 107 are reduced to release other body tissue 118 from opening 112, the vacuum is maintained in resection lumen 115.

Figure 12:
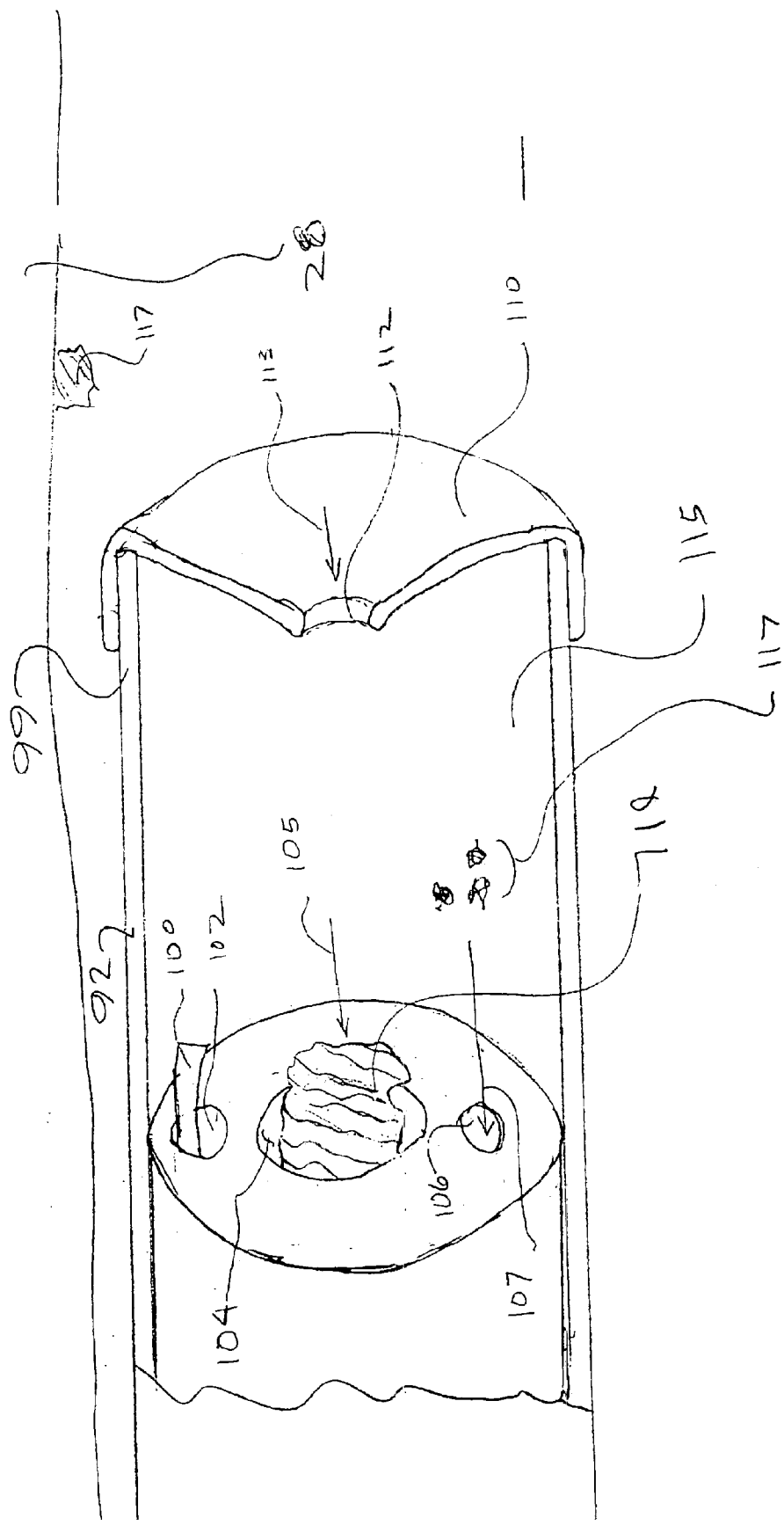
FIG. 12 illustrates a step where the vacuum draws the resected lymph node into a lumen to aspirate it from the patient.

FIG. 12 illustrates vacuum draw 105 pulling resected lymph node 71*l* into lumen 104 to aspirate resected lymph node 71*l* from the patient. After lymph node 71*l* is resected as illustrated in FIG. 11, vacuum draw 105 pulls resected lymph node 71*l* into lumen 104 and aspirates it from the patient and into the collector. Vacuum draw 107 maintains the vacuum in resection lumen 115 providing a backup vacuum draw in case resected lymph node 71*l* obstructs or reduces vacuum draw 105 while it is being aspirated. Vacuum draw 107 may also aspirate any resection byproducts 117 from the resection lumen 115. Lumens 104 and 102 are both in vacuum communication with the collector 96 of FIG. 4. The resected lymph node 71*l* is drawn through lumen 104 by vacuum draw 105 into the collector. Any resection byproducts 117 are also drawn into the collector through lumens 104 and 106. In an embodiment where collector 96 includes a plurality of collection chambers, resected lymph node 71*l* and any resection byproducts 117 are drawn into a selected collection chamber. In the embodiment where the collection chambers are indexed, the chamber with reference mark 2L would be selected. The collector may be quickly indexed by rotation to another chamber. As described in conjunction with FIG. 4, the collector may be disengaged from the electrosurgery device after receiving the resected lymph node 71*l*, and another collector may be engaged to receive other resected body tissue without removing the electrosurgery device from the patient. The electrosurgery device according to an embodiment of the invention allows a lymph node to be captured and to be resected with a single device.

Figure 13:
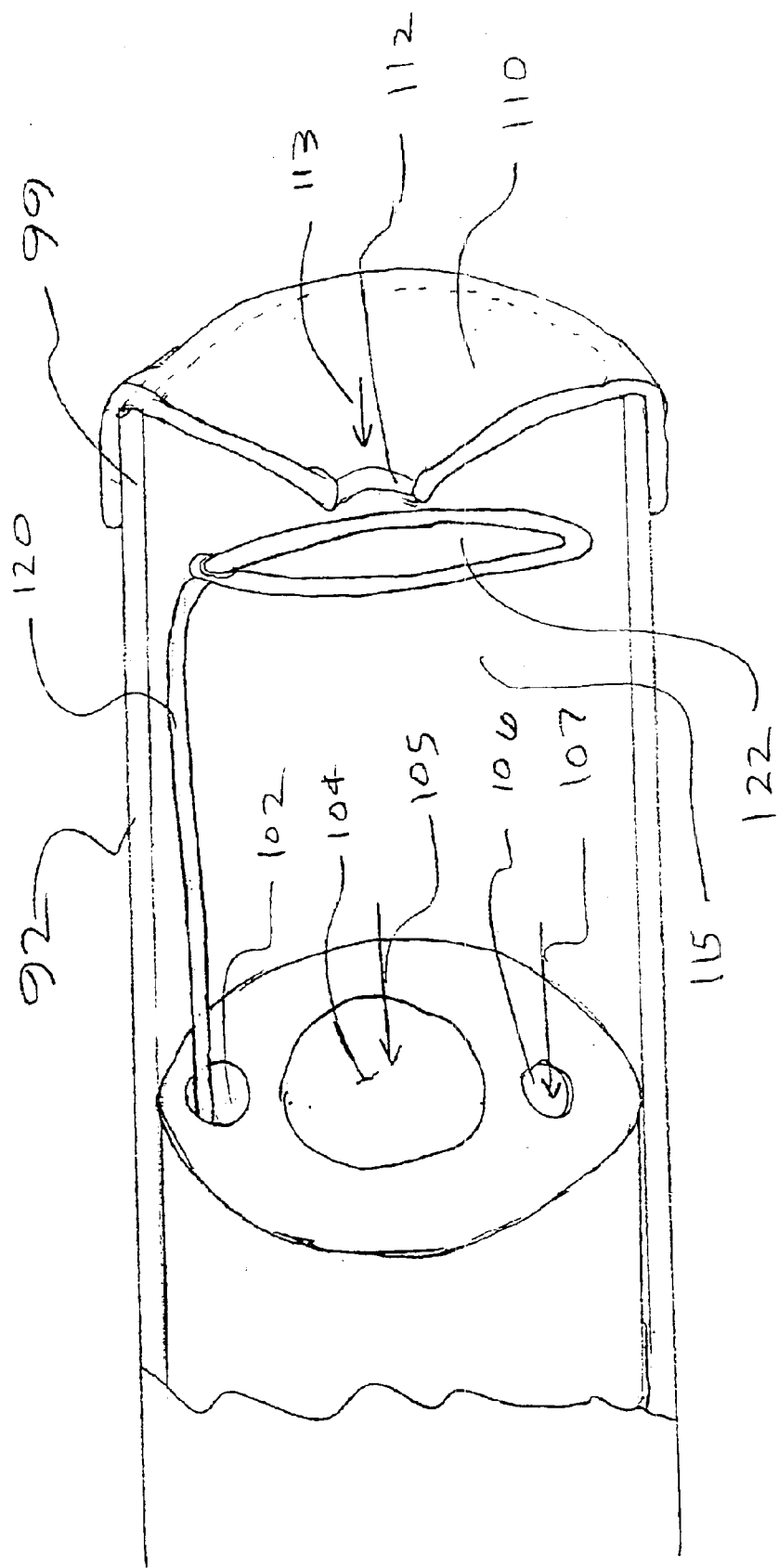
FIG. 13 is a side, partial longitudinal section view illustrating a distal tip of an electrical surgery device having a lasso-shaped active electrode, in accordance with an embodiment of the present invention.
Figure 14:
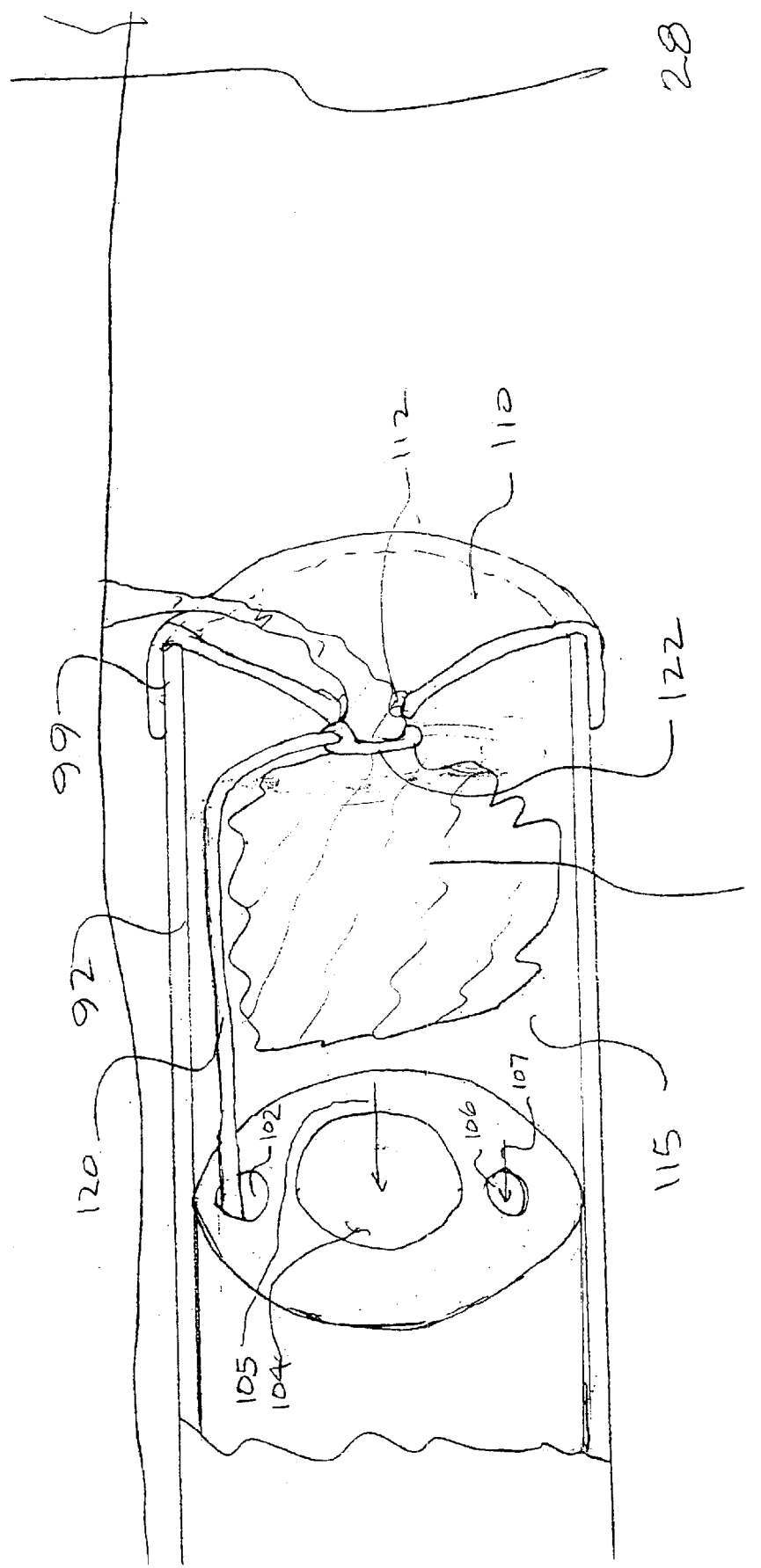
FIG. 14 illustrates the lasso-shaped active electrode loop of FIG. 13 cinched around a perimeter of the lymph node.

FIGS. 13 and 14 are side, partial longitudinal section views illustrating a distal tip 99 of an electrical surgery device having a lasso-shaped active electrode 120, in accordance with an embodiment of the present invention. A lasso-shaped active electrode 120 may be used in an alternative embodiment of the present invention to resect a lymph node. FIG. 13 illustrates lasso-shaped active electrode 120 arranged to form a loop 122 that may be cinched around a perimeter of lymph node 71*l*. Lymph node 71*l* is drawn into resection lumen 115 in the manner described in FIGS. 7–9. FIG. 14 illustrates loop 122 having been cinched around a perimeter of lymph node 71*l* by retraction of electrode 120. The retraction may be controlled by squeezing the activation device 94 of FIG. 4. Electrode 120 is activated to cut through tissue to resect lymph node 71*l* from other body tissue. Activation of the electrode may be by further squeezing the activation device, or by foot control unit 86 of FIG. 2. Lymph node 71*l* is aspirated from the patent in the manner described in FIG. 12. In an alternative embodiment, active electrode 120 may be a rigid loop that is retracted against a portion perimeter of lymph node 71*l* and activated to cut through the lymph node 71*l*.

Figure 15:
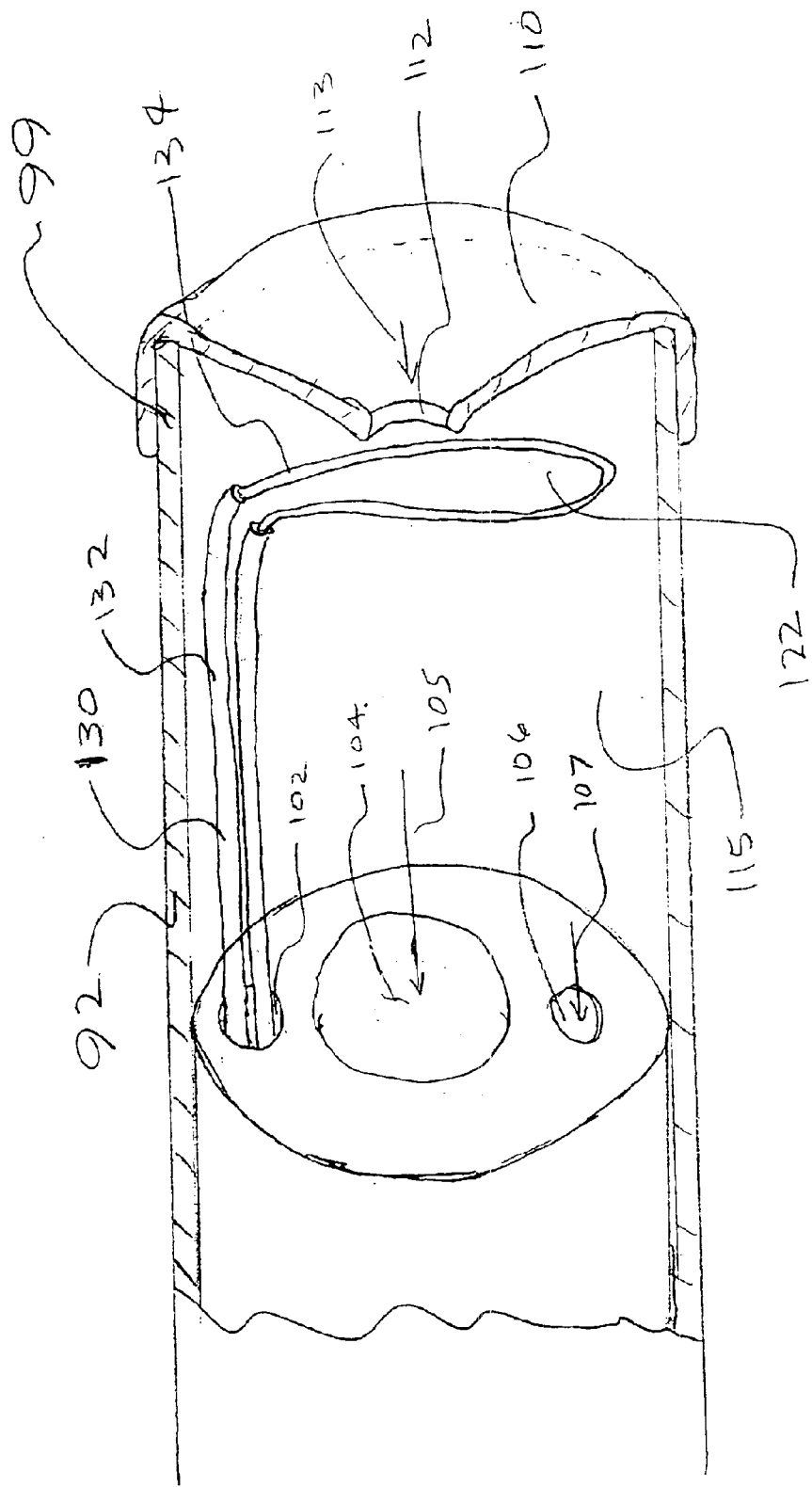
FIG. 15 is a side, partial longitudinal section view illustrating a distal tip of an electrical surgery device having a loop-shaped bipolar electrode, in accordance with an embodiment of the present invention.

FIG. 15 is a side, partial longitudinal section view illustrating a distal tip 99 of an electrical surgery device having a loop-shaped bipolar electrode 130, in accordance with an embodiment of the present invention. Bipolar electrode 130 includes insulation 132 and electrode 134. Insulation 132 electrically isolates bipolar electrode 130 from the electrosurgery device. Electrode 134 is formed into a loop 122 to snare lymph node 71*l* and perform the cutting. The bipolar electrode 130 is operated by an electrosurgery system substantially similar to the system illustrated in FIG. 3, except no ground electrode is required. The operation of loop-shaped bipolar electrode 130 is similar to the operation of electrode 120 described in conjunction with FIGS. 13 and 14.

Figure 16:
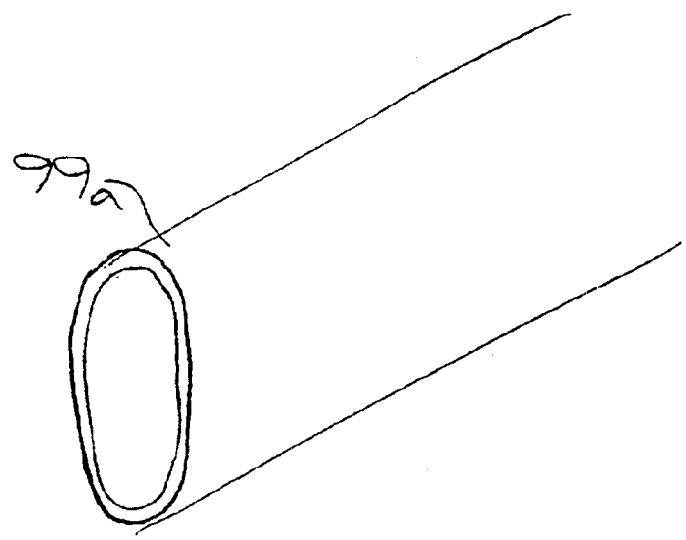
FIG. 16 illustrates an oval distal tip according to an embodiment of the invention.
Figure 17:
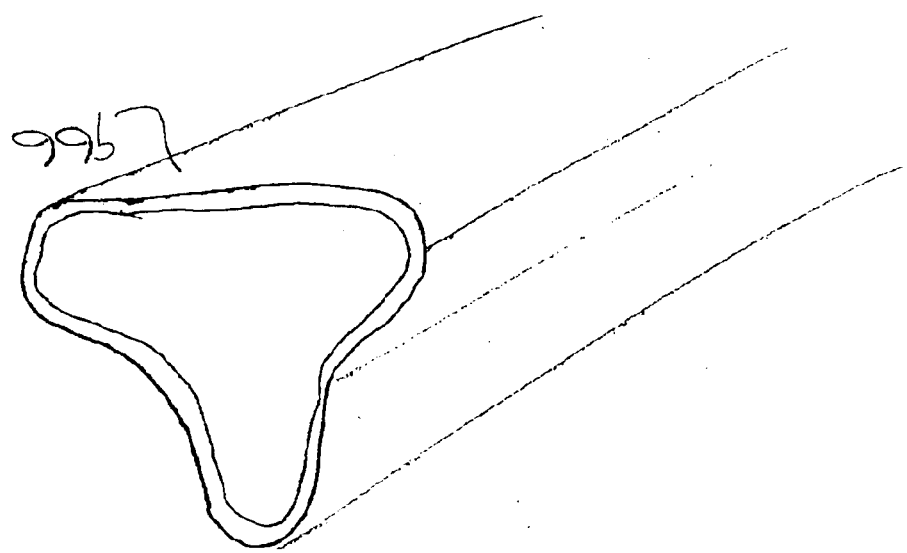
FIG. 17 illustrates a distal tip geometry designed to accommodate the trachea according to an embodiment of the invention.
Figure 18:
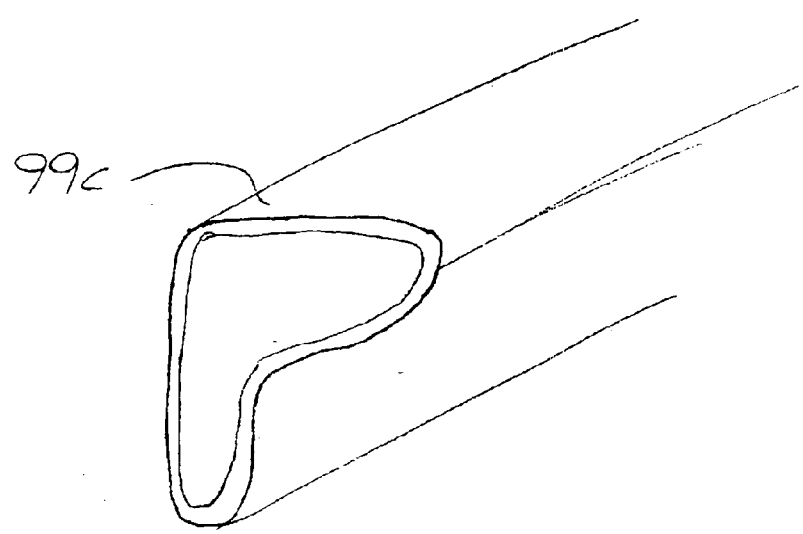
FIG. 18 illustrates an asymmetrical distal tip geometry according to an embodiment of the invention.
Figure 19:
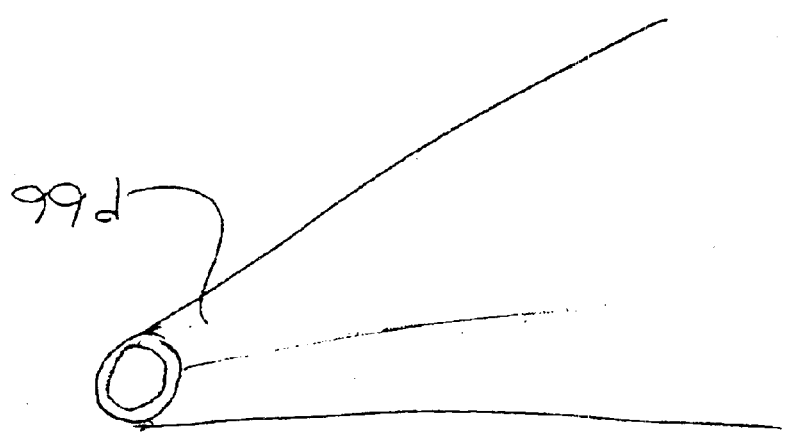
FIG. 19 illustrates a conical distal tip geometry according to an embodiment of the invention.

FIGS. 16–19 are perspective views illustrating alternative shapes of the distal tip 99 according to an embodiment of the invention. The distal tip 99 can be any shape, can lie in a single or in multiple planes, and can be at any angle to the longitudinal member 92 suitable for the intended use of the electrosurgery device. FIG. 16 illustrates an oval distal tip 99*a*. FIG. 17 illustrates a distal tip 99*b* having a geometry designed to accommodate the trachea. FIG. 18 illustrates a distal tip 99*c* having an asymmetrical geometry. FIG. 19 illustrates distal tip 99*d* having a conical geometry.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. A device for resecting selected body tissue from other body tissue at a site inside a patient and removing the selected body tissue, comprising:

an electrosurgery device having an electrode that cuts through tissue to resect the selected body tissue from the other body tissue;

a tubular member having a vacuum lumen that draws the selected body tissue into proximity with the electrode to permit the electrode to resect the selected body tissue from the other body tissue; and a collector having a plurality of collection chambers, each collection chamber being selectively communicable with the vacuum lumen to receive the resected body tissue.

2. A method of resecting a selected body tissue sample from other body tissue at a site inside a patient and removing the selected body tissue sample, comprising the steps of:

positioning a tubular member having a lumen adjacent to the selected body tissue;

creating a vacuum inside the lumen to draw the selected body tissue sample inside the lumen;

drawing the selected body tissue sample inside the lumen with a vacuum;

cutting through body tissue to resect the selected body tissue sample from the other body tissue with an electrosurgery device;

collecting the resected body tissue sample in a collection chamber of a collector;

indexing the collector to place a second collection chamber in communication with the lumen; and collecting a second body tissue sample in the second collection chamber.

3. The method of claim 2, including the further step of aspirating the selected body tissue from the patient out of another end of the lumen.

4. The method of claim 2, including the further step of drawing the selected body tissue with the vacuum through a compliant port that maintains a seal with the selected body tissue.

5. The method of claim 2, wherein the step of collecting the resected body tissue includes the further step of collecting resection byproducts.

6. A device for resecting a selected body tissue sample from other body tissue at a site inside a patient and removing the selected body tissue sample, comprising:

electrosurgery means for resecting the selected body tissue sample from the other body tissue;

vacuum directing means for drawing the selected body tissue sample into proximity with the electrosurgery means to permit the electrosurgery means to resect the selected body tissue sample from the other body tissue; and collection means for receiving the resected body tissue, the collection means configured with a plurality of collection storage means each configured to be in selective communication with the vacuum directing means and further configured to each store a body tissue sample.

7. The device of claim 1, further comprising a compliant port disposed on the tubular member at its distal end configured to maintain a seal with the selected body tissue.

8. The device of claim 7, wherein the compliant port is configured with an adjustable aperture.

9. The device of claim 8, wherein the adjustable aperture is resiliently adjustable in response to the size of the selected body tissue.

10. The device of claim 1, wherein the electrode has a distal end and wherein the electrode distal end is disposed within the lumen while resecting body tissue.

11. The device of claim 1, wherein the collector is configured to be indexed between a plurality of positions in which a corresponding plurality of collection chambers are each selectively in communication with the vacuum lumen.

12. The device of claim 1, further comprising a secondary vacuum lumen.

* * * * *